United States Patent
Jones et al.

(10) Patent No.: US 6,428,558 B1
(45) Date of Patent: Aug. 6, 2002

(54) ANEURYSM EMBOLIZATION DEVICE

(75) Inventors: Donald K. Jones, Lauderhill; Vladimir Mitelberg, Aventura, both of FL (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/505,231

(22) Filed: Feb. 16, 2000

Related U.S. Application Data

(60) Provisional application No. 60/123,575, filed on Mar. 10, 1999.

(51) Int. Cl.⁷ .............................................. A61B 17/00
(52) U.S. Cl. ....................... 606/200; 606/151
(58) Field of Search ............... 606/108, 200, 606/151, 191, 127, 114, 159; 604/105, 107

(56) References Cited

U.S. PATENT DOCUMENTS

| | | |
|---|---|---|
| 4,517,979 A | 5/1985 | Pecenka |
| 4,994,069 A | 2/1991 | Ritchart et al. |
| 5,151,105 A | 9/1992 | Kwan-Gett |
| 5,334,210 A | 8/1994 | Gianturco |
| 5,417,708 A | 5/1995 | Hall et al. |
| 5,522,822 A | 6/1996 | Phelps et al. |
| 5,527,338 A | 6/1996 | Purdy |
| 5,645,558 A | 7/1997 | Horton |
| 5,649,950 A | 7/1997 | Bourne et al. |
| 5,733,294 A | 3/1998 | Forber et al. |
| 5,919,224 A | 7/1999 | Thompson et al. |
| 6,146,396 A * | 11/2000 | Konya et al. ............... 606/200 |
| 6,221,086 B1 * | 4/2001 | Forber ........................ 606/151 |

FOREIGN PATENT DOCUMENTS

| | | |
|---|---|---|
| EP | 0 882 428 | 9/1998 |
| WO | WO 99/12484 | 8/1998 |
| WO | WO 00/51500 | 3/2000 |

\* cited by examiner

*Primary Examiner*—Kevin Truong

(57) ABSTRACT

An aneurysm embolization device which may be used to occlude a blood vessel or aneurysm. The device has a plurality of support struts which form a substantially ellipsoidal shape. The support struts are preferably formed from a nickel-titanium alloy, such as nitinol, which has superelastic characteristics. A mesh sleeve is disposed over the support struts. The mesh sleeve is preferably formed of a thrombogenic material, such as polyurethane, so as to encourage the formation of blood clots and scar tissue to permanently occlude the vessel.

22 Claims, 2 Drawing Sheets

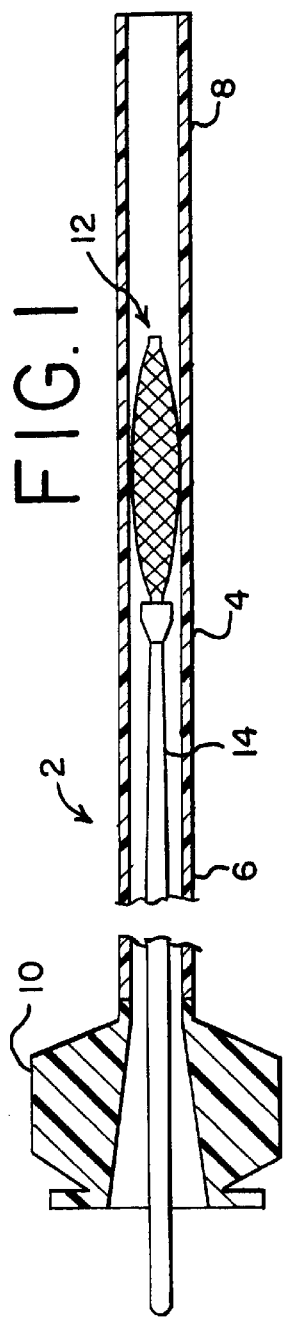
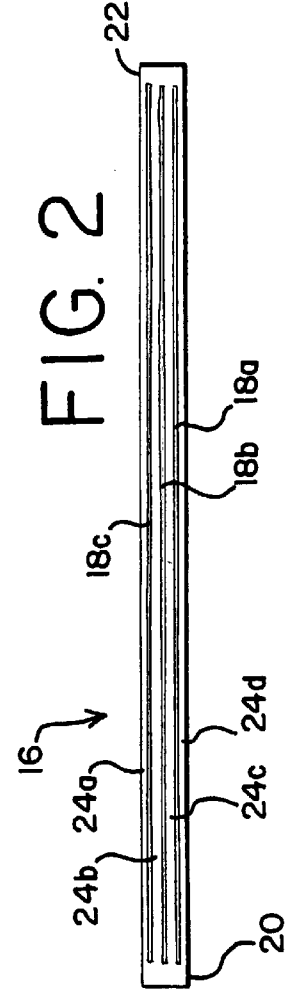
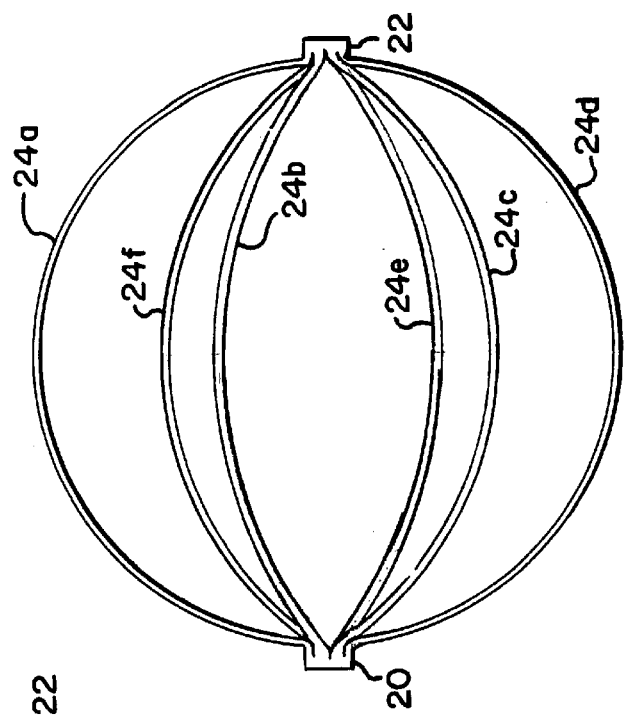

ANEURYSM EMBOLIZATION DEVICE

CROSS-REFERENCE TO A RELATED APPLICATION

This application claims the benefit of U.S. Provisional Application No. 60/123,575 filed Mar. 10, 1999, the disclosure of which is incorporated herein by reference.

BACKGROUND OF THE INVENTION

1. Field of the Invention

This invention relates generally to vascular occlusion devices and particularly to a vascular occlusion device which self-expands to occlude a blood vessel or an aneurysm.

2. Description of the Prior Art

Medical devices adapted for implantation in the vasculature of the human body are well known and commercially available. Such devices are typically used to permanently occlude blood flow in a blood vessel or seal an aneurysm to prevent the catastrophic results of it rupturing. A variety of occlusion devices are known to the art.

U.S. Pat. No. 4,517,979 to Pecenka discloses a detachable balloon catheter. The balloon catheter is inserted into a blood vessel and inflated with a fluid. When the catheter is withdrawn, the balloon section detaches and an internal mechanism seals the balloon to prevent the outflow of fluid. The balloon is typically fabricated from either latex or silicone rubber.

U.S. Pat. No. 4,994,069 to Richart, et al., discloses a vaso-occlusion coil. A coiled wire is stretched and threaded through a catheter to a selected site within a vessel. When the wire is released from the distal end of the catheter, it resumes its substantially space-filling shape.

U.S. Pat. No. 5,334,210 to Gianturco discloses a vascular occlusion assembly comprising a foldable material occlusion bag having an expanded diamond shape and an elongated flexible filler member which is inserted in the internal cavity of the bag.

U.S. Pat. No. 5,527,338 to Purdy discloses an "umbrella" of expansion members extending from a lead element and a fabric web extending between the expansion members. A trailing element is connected to the lead element by at least one fiber and is potentially used to assist in deploying the device. The tips of the support members serve to anchor the device within the vessel.

SUMMARY OF THE INVENTION

In accordance with the present invention, there is an embolization device deployment system which includes a catheter, having a proximal end, a distal end, and a lumen extending therethrough. The embolization device deployment system further includes an embolization device having a plurality of arcuate support struts which are connected to each other to form a structure of a substantially ellipsoidal configuration. The embolization device further includes a mesh sleeve disposed over and attached to the support struts. The embolization device is slidingly disposed within the lumen at the distal end of the catheter. The embolization device deployment system further includes a hub, having a lumen extending therethrough, which is mounted on the proximal end of the catheter such that the lumen of the hub communicates with the lumen of the catheter. The embolization device deployment system further includes a pusher mechanism which is disposed through the lumen of the hub and the lumen of the catheter, and which is used to displace the embolization device from within the lumen at the distal end of the catheter to thereby deploy the embolization device within a blood vessel.

In accordance with another aspect of the present invention, the support struts have a proximal end and a distal end, are attached at at least one end, and are biased outwardly to form a substantially ellipsoidal structure.

In accordance with another aspect of the present invention, there is an embolization device deployment system which includes a catheter, having a proximal end, a distal end, and a lumen extending therethrough. The embolization device deployment system further includes an embolization device having a plurality of arcuate support struts. The support struts are attached at the proximal and distal ends and biased outwardly to form a substantially ellipsoidal structure. The embolization device further includes a mesh sleeve disposed over and attached to the support struts. The embolization device is slidingly disposed within the lumen of the distal end of the catheter. The embolization device deployment system further includes a hub, having a lumen extending therethrough, which is mounted on the proximal end of the catheter such that the lumen of the hub communicates with the lumen of the catheter. The embolization device deployment system further includes a pusher mechanism which is disposed through the lumen of the hub and the lumen of the catheter, and which is used to displace the embolization device from within the lumen at the distal end of the catheter to thereby deploy the embolization device within a blood vessel.

In accordance with another aspect of the present invention, there is an embolization device deployment system which includes a catheter, having a proximal end, a distal end, and a lumen extending therethrough. The embolization device deployment system further includes an embolization device having a plurality of arcuate support struts. The support struts are formed from a tube having a tubular wall and a lumen extending therethrough. The tube also has a proximal end, a distal end, and a plurality of longitudinal cuts through the wall of the tube. The cuts extend from a point near the proximal end of the tube to a point near the distal end of the tube. The support struts are biased outwardly to form a substantially ellipsoidal structure. The embolization device further includes a mesh sleeve disposed over and attached to the support struts. The embolization device is slidingly disposed within the lumen of the distal end of the catheter. The embolization device deployment system further includes a hub, having a lumen extending therethrough, which is mounted on the proximal end of the catheter such that the lumen of the hub communicates with the lumen of the catheter. The embolization device deployment system further includes a pusher mechanism which is disposed through the lumen of the hub and the lumen of the catheter, and which is used to displace the embolization device from within the lumen at the distal end of the catheter to thereby deploy the embolization device within a blood vessel.

In accordance with still another aspect of the present invention, the support struts are formed from a superelastic alloy and said mesh sleeve is formed from a thrombogenic material. The alloy is preferably formed from nickel and titanium. The composition of the alloy is preferably at least about 51% nickel and at least about 44% titanium.

In accordance with another aspect of the present invention, the thrombogenic material is formed of polyurethane, the support struts are coated with a layer of polyurethane material, and the mesh sleeve is heat fused to the support struts. The layer of polyurethane material preferably includes a radiopaque compound, such as tantalum.

BRIEF DESCRIPTION OF THE DRAWINGS

FIG. 1 is a longitudinal cross-section of an embolization device deployment system;

FIG. 2 is a plain view of a tube used to form the embolization device;

FIG. 3 is a plain view of a tube used to form the embolization device after column force has been applied;

DESCRIPTION OF A PREFERRED EMBODIMENT

Figure 4:
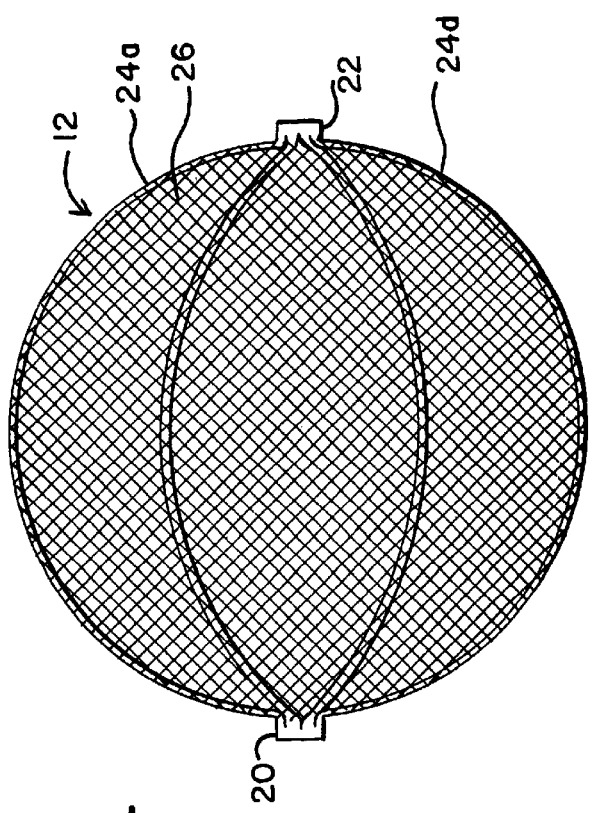
FIG. 4 is a plain view of the embolization device after it has been fully assembled.

FIG. 1 generally illustrates an embolization device deployment system 2 which is comprised of a catheter 4, having a proximal end 6 and a distal end 8, a hub 10 attached to the proximal end 6 of the catheter 4, and an embolization device 12 disposed within the lumen of the distal end 8 of the catheter 4. The lumen of the hub 10 is in fluid communication with the lumen of the catheter 4. A pusher mechanism 14 is threaded through the lumen of the hub 10 and into the lumen of the catheter 4.

FIGS. 2, 3, and 4 show the basic steps in the formation of the embolization device 12. FIG. 2 shows a section of metallic tubing 16 with a plurality of longitudinal cuts 18a, 18b, 18c through the wall of the tubing 16. As can be appreciated, the perspective of FIG. 2 shows three cuts, with three more on the non-visible side. Each cut begins near the proximal end of the tubing and ends near the distal end of the tubing, with the result being the formation of a proximal collar 20, a distal collar 22, and a plurality of support struts 24a, 24b, 24c, 24d. Two additional support struts, 24e and 24f, are formed on the non-visible side of the tube. A column force is applied at the ends of the metallic tubing 16, causing the support struts 24a–24f to bias outwardly, as shown in FIG. 3. In the preferred embodiment, the tubing is formed of a nickel-titanium alloy, or nitinol, which can be heat treated to allow the tubing to retain a substantially ellipsoidal shape. The support struts 24a–24f are preferably coated with a layer of polyurethane material. As shown in FIG. 4, a mesh sleeve 26 is fit over the support struts 24a–24f, and the mesh sleeve is heat fused to the underlying support struts. The mesh sleeve 26 is formed form a thrombogenic material, preferably polyurethane, which promotes the formation of blood clots.

Figure 5:
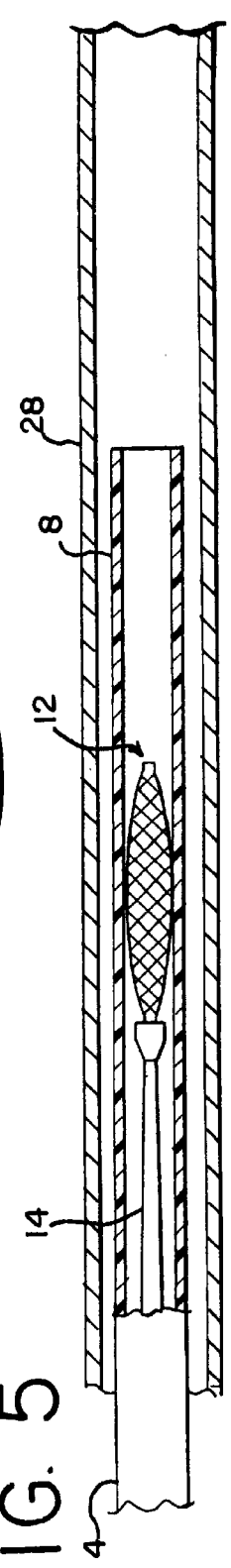
FIG. 5 is a partially sectioned view of the embolization device in the catheter prior to deployment; and, FIG. 6 is a partially sectioned view of the embolization device after being deployed in a blood vessel.
Figure 6:
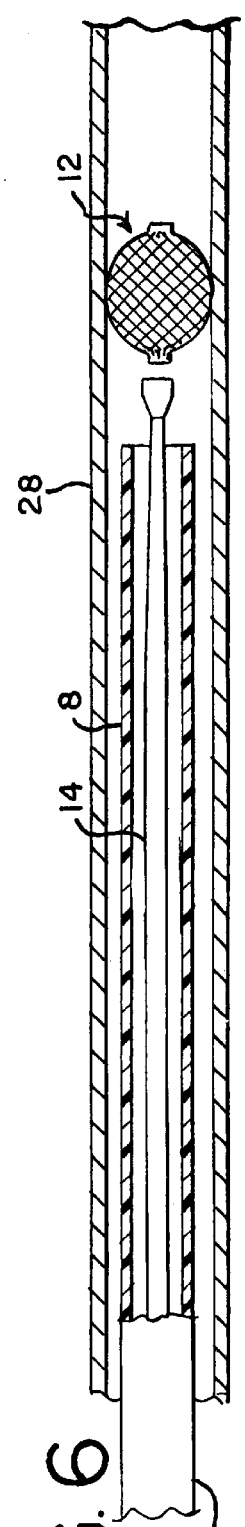

FIGS. 5 and 6 depict the deployment of an embolization device within a blood vessel. As shown in FIG. 5, the embolization device 12 is radially compressed into a more ellipsoidal shape before being disposed within the distal end 8 of the catheter 4. The catheter 4 is then inserted within a blood vessel 28. When the catheter 4 reaches the point of deployment, the embolization device 12 is slidingly deployed from within the distal end 8 of the catheter 4 as shown in FIG. 6. Preferably, a pusher mechanism 14 is used to deploy the embolization device 12 by pushing it out the distal end 8 of the catheter 4; however, a variety of deployment methods are known to those skilled in the art.

In order to fit within the catheter, the embolization device must be compressed or collapsed into a more ellipsoidal shape. Once deployed, the embolization device anchors itself by applying sufficient radial force against the wall of the blood vessel or aneurysm. The superelastic property of nitinol allows the support struts of the embolization device to undergo considerable compression, yet return to their original shape when the compression force is removed. In the preferred embodiment, a formulation of nitinol comprising about 51% to 56% nickel and about 44% to 49% titanium is used. Preferably, the nitinol formulation comprises 55.7% nickel and 44.3% titanium.

Because the embolization device anchors in the aneurysm by applying radial force against the aneurysm wall, the embolization device is typically sized to fit the blood vessel, with the diameter of the embolization device being in the range of about 1 mm to 100 mm. As can be appreciated, the size of the support struts typically depend on the size of the embolization device, with the range being between about 0.0015 inches and 0.025 inches. In the preferred embodiment, the embolization device after deployment is substantially spheroidal; however, a substantially ellipsoidal shape could perform the same function. The embolization device preferably has six support struts, but a greater or lesser number could be used to achieve a more or less circular cross-section. A layer of polyurethane material, between about 0.00001 inches and 0.001 inches, is applied to the support struts. Preferably, the thickness of the layer of polyurethane material is 0.0005 inches. The primary purpose of the layer of polyurethane material is to aid in heat fusing the mesh sleeve to the support struts. However, a radiopaque compound, such as tungsten or, preferably, tantalum, may be added to the polyurethane to assist in positioning the embolization device.

The mesh sleeve is specifically designed to cover the neck of an aneurysm to prevent blood flow into the aneurysm. This configuration greatly improves the ability to treat aneurysms with respect to conventional coils that require dense packing of the aneurysm to achieve the same desired effect. The mesh sleeve can be formed from a variety of polymeric materials, including polyether and polyurethane. In the preferred embodiment, the mesh sleeve is formed of a polyurethane material, which has thrombogenic properties, to encourage thrombus and scar tissue formation to aid in long term occlusion stability. It is also possible that the mesh sleeve, normally made of a permeable or semi-permeable material, may be formed from a more solid material, such as silicone, to create a non-permeable membrane.

As is apparent, there are numerous modifications of the preferred embodiment described above that will be readily apparent to one skilled in the art. These include variations and modifications of the support struts, including the use of wound wire or coils. Various materials could also be used to form the support struts, including polymeric materials formed from nylon, polyester, or polycarbonate. Also, there are obviously variations of the mesh sleeve, including the introduction of bioactive agents or materials to increase the thrombogenicity of the device. These modifications would be apparent to those having ordinary skill in the art to which this invention relates and are intended to be within the scope of the claims that follow.

That which is claimed is:

1. An embolization device deployment system comprising:

a catheter having a proximal end, a distal end, and a lumen extending throughout the length of the catheter;

an embolization device comprising a plurality of arcuate support struts, said support struts being connected to each other to form a structure of a substantially ellipsoidal configuration, said embolization device further comprising a mesh sleeve disposed over and attached to said support struts, said embolization device being slidingly disposed within the lumen at the distal end of the catheter;

a hub having a lumen extending therethrough, said hub being mounted on the proximal end of the catheter and the lumen of the hub communicating with the lumen of the catheter; and, a pusher mechanism disposed through the lumen of the hub and the lumen of the catheter, said pusher mechanism being used to displace said embolization device from within the lumen at the distal end of the catheter to thereby deploy said embolization device within a blood vessel.

2. An embolization device deployment system as defined in claim 1, wherein said support struts have a proximal end and a distal end, said supports struts being attached at least one end and biased outwardly to form a substantially ellipsoidal structure.

3. An embolization device deployment system as defined in claim 2, wherein said support struts are formed from a superelastic alloy and said mesh sleeve is formed from a thrombogenic material.

4. An embolization device deployment system as defined in claim 3, wherein said alloy is formed from nickel and titanium.

5. An embolization device deployment system as defined in claim 4, wherein said alloy is comprised of at least about 51% nickel and at least about 44% titanium.

6. An embolization device deployment system as defined in claim 3, wherein said thrombogenic material is comprised of polyurethane, said support struts are coated with a layer of polyurethane material, and said mesh sleeve is heat fused to said support struts.

7. An embolization device deployment system as defined in claim 6, wherein said layer of polyurethane material includes a radiopaque compound.

8. An embolization device deployment system as defined in claim 7, wherein said radiopaque compound is comprised of tantalum.

9. An embolization device deployment system comprising:

a catheter having a proximal end, a distal end, and a lumen extending throughout the length of the catheter;

an embolization device comprising a plurality of arcuate support struts, said support struts having a proximal end and a distal end, said supports struts being attached at the proximal and distal ends and biased outwardly to form a substantially ellipsoidal structure, said embolization device further comprising a mesh sleeve disposed over and attached to said support struts, said embolization device being slidingly disposed within the lumen of the distal end of the catheter;

a hub having a lumen extending therethrough, said hub being mounted on the proximal end of the catheter and the lumen of the hub communicating with the lumen of the catheter; and, a pusher mechanism disposed through the lumen of the hub and the lumen of the catheter, said pusher mechanism being used to displace said embolization device from within the lumen at the distal end of the catheter to thereby deploy said embolization device within a blood vessel.

10. An embolization device deployment system as defined in claim 9, wherein said support struts are formed from a superelastic alloy and said mesh sleeve is formed from a thrombogenic material.

11. An embolization device deployment system as defined in claim 10, wherein said alloy is comprised of nickel and titanium.

12. An embolization device deployment system as defined in claim 11, wherein said alloy is comprised of at least about 51% nickel and at least about 44% titanium.

13. An embolization device deployment system as defined in claim 10, wherein said thrombogenic material is comprised of polyurethane, said support struts are coated with a layer of polyurethane material, and said mesh sleeve is heat fused to said support struts.

14. An embolization device deployment system as defined in claim 13, wherein said layer of polyurethane material includes a radiopaque compound.

15. An embolization device deployment system as defined in claim 14, wherein said radiopaque compound is comprised of tantalum.

16. An embolization device deployment system comprising:

a catheter having a proximal end, a distal end, and a lumen extending throughout the length of the catheter;

an embolization device comprising a plurality of arcuate support struts, said support struts being comprised of a tube, said tube having a tubular wall and a lumen extending therethrough, said tube further having a proximal end, a distal end, and a plurality of longitudinal cuts through the wall of the tube, said cuts extending from a point near the proximal end of the tube and extending to a point near the distal end of the tube, said support struts being biased outwardly to form a substantially ellipsoidal structure, said embolization device further comprising a mesh sleeve disposed over and attached to said support struts, said embolization device being slidingly disposed within the lumen of the distal end of the catheter;

a hub having a lumen extending therethrough, said hub being mounted on the proximal end of the catheter and the lumen of the hub communicating with the lumen of the catheter; and, a pusher mechanism disposed through the lumen of the hub and the lumen of the catheter, said pusher mechanism being used to displace said embolization device from within the lumen at the distal end of the catheter to thereby deploy said embolization device within a blood vessel.

17. An embolization device deployment system as defined in claim 16, wherein said support struts are formed from a superelastic alloy and said mesh sleeve is formed from a thrombogenic material.

18. An embolization device deployment system as defined in claim 17, wherein said alloy is comprised of nickel and titanium.

19. An embolization device deployment system as defined in claim 18, wherein said alloy is comprised of at least about 51% nickel and at least about 44% titanium.

20. An embolization device deployment system as defined in claim 17, wherein said thrombogenic material is comprised of polyurethane, said support struts are coated with a layer of polyurethane material, and said mesh sleeve is heat fused to said support struts.

21. An embolization device deployment system as defined in claim 20, wherein said layer of polyurethane material includes a radiopaque compound.

22. An embolization device deployment system as defined in claim 21, wherein said radiopaque compound is comprised of tantalum.

* * * * *